United States Patent
Plaian et al.

(10) Patent No.: US 12,121,301 B2
(45) Date of Patent: Oct. 22, 2024

(54) LINE-SCANNING CONFOCAL INSPECTION APPARATUS

(71) Applicant: CenterVue S.P.A., Padua (IT)

(72) Inventors: Andrei Plaian, Noventa Padovana (IT); Federico Manzan, San Pietro di Feletto (IT); Marco D'Aguanno, Albignasego (IT); Irene Mogentale, Due Carrare (IT)

(73) Assignee: Center Vue S.p.A., Padua (IT)

( * ) Notice: Subject to any disclaimer, the term of this patent is extended or adjusted under 35 U.S.C. 154(b) by 496 days.

(21) Appl. No.: 17/627,375

(22) PCT Filed: Aug. 27, 2020

(86) PCT No.: PCT/EP2020/074005
§ 371 (c)(1),
(2) Date: Jan. 14, 2022

(87) PCT Pub. No.: WO2021/047917
PCT Pub. Date: Mar. 18, 2021

(65) Prior Publication Data
US 2022/0257113 A1    Aug. 18, 2022

(30) Foreign Application Priority Data

Sep. 10, 2019  (IT) .................. 102019000016016

(51) Int. Cl.
*A61B 3/10*    (2006.01)
*A61B 3/12*    (2006.01)

(52) U.S. Cl.
CPC .............. *A61B 3/1025* (2013.01); *A61B 3/12* (2013.01)

(58) Field of Classification Search
CPC .... A61B 3/1025; A61B 3/12; G02B 21/0028; G02B 21/0032; G02B 21/0036
(Continued)

(56) References Cited

U.S. PATENT DOCUMENTS 7,331,669 B2   2/2008 Elsner
10,061,111 B2* 8/2018 Hillman ............. G02B 21/0052
(Continued)

OTHER PUBLICATIONS

International Searching Authority: European Patent Office Search Report and Written Opinion for corresponding International Patent Application No. PCT/EP2020/074005, dated Dec. 9, 2020, 12 pages.

*Primary Examiner* — Tuyen Tra
(74) *Attorney, Agent, or Firm* — Patterson Intellectual Property Law, PC

(57) ABSTRACT

The present invention relates to an apparatus for inspecting the ocular fundus that comprises: —an illuminator (1) adapted to provide an illuminating light beam (IL) to illuminate a portion of said biological tissue, said illuminating beam being shaped so that at least a portion of said illuminating beam has a line-shaped section; —one or more lenses (2, 4, 7) to focus said illuminating beam (IL) on said biological tissue, during operation of said apparatus said illuminating beam illuminating a line-shaped region (5B) of said biological tissue; —a scanning assembly (3) adapted to perform optical scans of said biological tissue by cyclically moving the illuminating beam (IL) projected by said illuminator on said biological tissue, along a scanning direction (DS) substantially perpendicular to a main extension direction (AE) of the region (5B) of biological tissue illuminated by said illuminating beam; —acquisition means (6) adapted to receive reflected light (R) from said biological tissue to acquire images of said biological tissue or to allow an observer to observe said biological tissue. Said scanning assembly (3) comprises: —a fixed support (33); —a first oscillating group (31) comprising a first mobile arm (312) and a minor (311) fixed to said mobile arm and adapted to receive said illuminating beam (IL), said first mobile arm being linked with said fixed support through one or more
(Continued)

Figure 1:
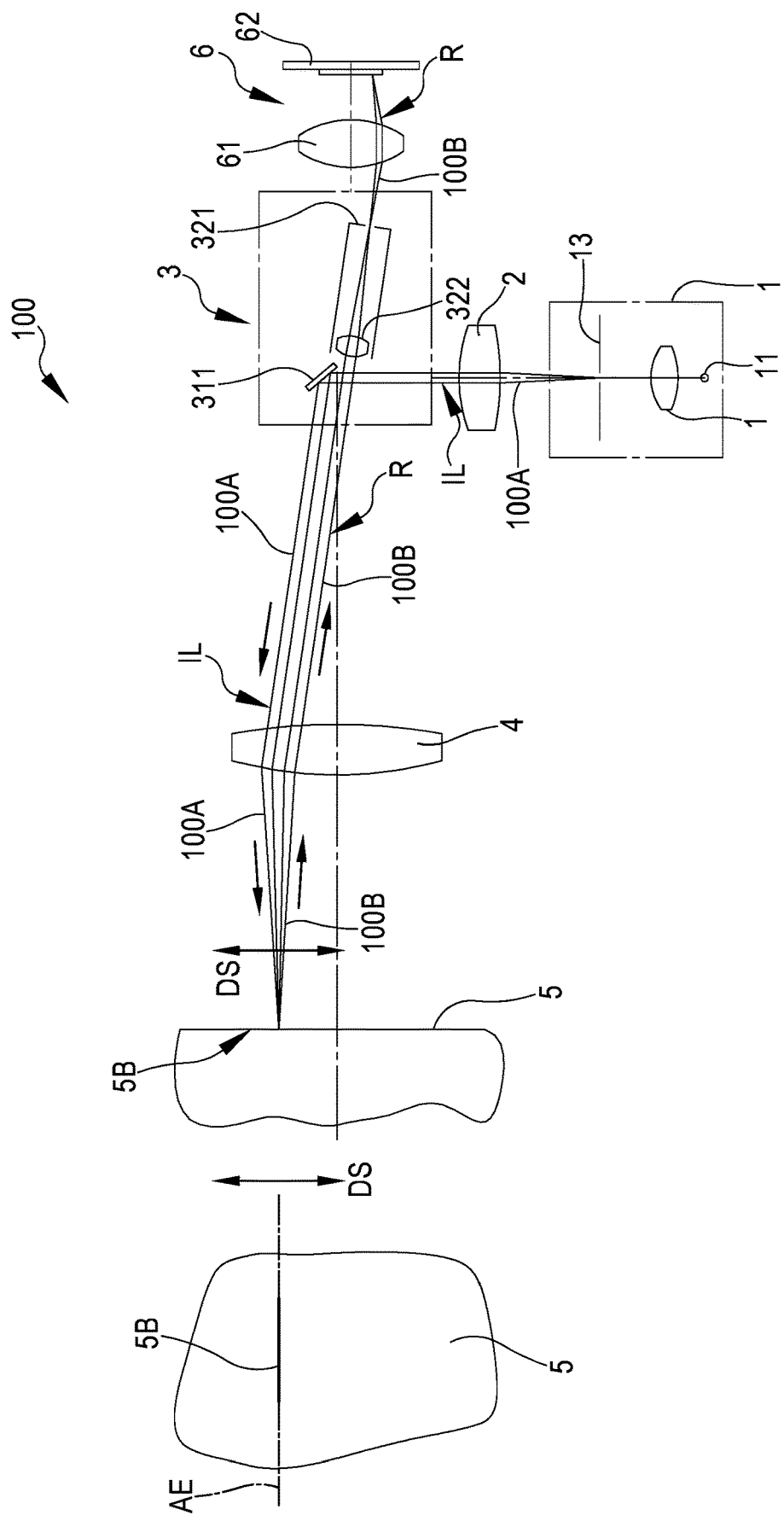

first joints (A1) that allow the rotation of said first mobile arm about a rotation axis (B1); —a second oscillating group (32) comprising a second mobile arm (323) and a first lens (322) and a diaphragm (321) comprising a slot-shaped opening (321A) fixed to said mobile arm and adapted to receive the reflected light (R) from said biological tissue, said second mobile arm being linked with said fixed support through one or more second joints (A2) that allow the rotation of the said first mobile arm about a rotation axis (B1); —mechanical transmission means (34) adapted to mutually link said first and second mobile arm, said mechanical transmission means being configured to synchronize the oscillating movements of said first and second arm.

12 Claims, 9 Drawing Sheets

(58) Field of Classification Search
USPC .................................................. 351/200, 205
See application file for complete search history.

(56) References Cited

U.S. PATENT DOCUMENTS

| | | | |
|---|---|---|---|
| 11,726,043 B2* | 8/2023 | Vasdekis | G02B 21/0064 |
| | | | 348/79 |
| 12,053,261 B2* | 8/2024 | Fox | A61B 5/445 |
| 2015/0192461 A1 | 7/2015 | Chen | |

* cited by examiner

LINE-SCANNING CONFOCAL INSPECTION APPARATUS

The present invention relates to a line-scanning confocal inspection apparatus.

The use of line-scanning confocal inspection apparatus for observing or acquiring images of translucent objects, in particular of biological tissues, such as the ocular fundus or a portion of skin of a patient, is widely known.

In general, these inspection apparatuses scan an object with a light beam that illuminates a very narrow line-shaped zone thereof. The light reflected by the object is sent to a diaphragm having a slit-shaped opening. The light passing through the diaphragm is then sent to suitable acquisition means that allow observation of the object or acquisition of images thereof.

Line-scanning confocal inspection apparatus capable of directly producing a two-dimensional image of the object are of particular interest. This two-dimensional image can be observed directly by an operator through an ocular or acquired through a two-dimensional sensor.

U.S. Pat. No. 3,547,512A describes a line-scanning confocal inspection apparatus that uses a mobile assembly containing two diaphragms, each having a slit-shaped opening, and a mirror, moved synchronously. Both diaphragms are optically conjugated with the surface of the object observed through an objective. A diaphragm selects a linear portion of illuminating beam. This portion of illuminating beam is scanned onto the object due to the movement of this diaphragm. The other diaphragm selects a portion of reflected light from the object on the related focal plane and filters parasitic light coming from other planes.

The solution proposed in the above-mentioned patent document has some problems.

In this inspection apparatus, separation between illuminating beam and reflected light from the object is obtained at the edge of an illuminated mirror. Scattering of illuminating light at this edge can cause reflections or artefacts in the images of biological tissue.

A further drawback of the inspection apparatus consists in that it is necessary to provide a completely homogenous illuminating beam to obtain satisfactory homogeneity in the illumination of the object. Experience has shown how this requirement is somewhat difficult to achieve on an industrial scale.

A further drawback consists in that the inspection apparatus includes compromise optical solutions that offer satisfactory performance only if the field of vision is relatively narrow. Patent documents U.S. Pat. Nos. 4,241,257, 73,311, 669, EP2392915, WO2016/037984A1 describe further examples of confocal devices with line-scanning confocal inspection apparatus.

Although at least partly overcoming the drawbacks of the solution illustrated above, these solutions still have some problematic aspects.

U.S. Pat. No. 4,241,257 describes a line-scanning inspection apparatus comprising three mobile mirrors and a fixed confocal diaphragm, having a slot-shaped opening.

A first mobile mirror scans the illuminating light at the object to be observed. A second mobile mirror de-scans the reflected light from the object to convert it into a fixed light beam. The aforesaid confocal diaphragm filters the fixed light beam to remove any parasitic light. Finally, a third mobile mirror re-scans the light beam filtered by the confocal diaphragm to generate a two-dimensional image of the object.

The solution proposed by this patent document has some limits with regard to the quality of the confocal filter process of the reflected light from the object. In certain conditions, the images of the object acquired can thus have low brightness contrast or artefacts.

U.S. Pat. No. 7,331,669 describes a solution similar to the previous solution in which a polygonal mirror, capable of carrying out a rotation movement, is used to reflect the light passing through several times.

A first face of the polygonal mirror scans the illuminating light on the object while a second face de-scans the reflected light from the object to convert it into a fixed beam. After passing through a fixed confocal slot, the reflected light is re-scanned by a third face of the polygonal mirror to produce a two-dimensional image.

This inspection apparatus is very complex from a construction viewpoint and has a large number of components. For example, a total of seven mirrors arranged in series are present in the optical path of the reflected light from the object. Given the large number of optical components, the minimum deterioration of their surface (for example due to dirt or phenomena of corrosion) can significantly reduce the quality of the image acquired. Moreover, the overall costs to produce this solution on an industrial scale are very high.

Patent documents EP2392915 and WO2016/037984A1 describe line-scanning inspection apparatus that use an oscillating mirror with two mutually opposite reflecting surfaces.

The illuminating light is reflected from a first surface of the oscillating mirror that carries out the scan on the surface of the object to be observed.

The reflected light from the object is de-scanned by the same surface of the oscillating mirror and is converted into a fixed light beam. This light beam is conveyed along an optical path in which suitable mirrors, lenses and a fixed confocal diaphragm having a slot-shaped opening are arranged.

Following the filtering carried out by the aforesaid confocal diaphragm, the reflected light from the object observed is returned to the other surface of the oscillating mirror, which re-scans it to produce a two-dimensional image, then acquired with suitable acquisition means.

Against performances that are often unsatisfactory, the inspection apparatus described in these last-mentioned patent documents are characterised by complex construction and are very costly to produce on an industrial scale.

The main aim of the present invention to provide an apparatus for inspecting the ocular fundus, of line-scanning confocal type, which allows the drawbacks of the prior art set forth above to be overcome.

Within this aim, an object of the present invention is to provide an inspection apparatus that offers high performance while being considerably compact and of simple construction.

A further object of the present invention is to provide an inspection apparatus that is able to effectively filter parasitic light or undesirable reflections along the optical imaging path of the reflected light from the biological tissue.

A further object of the present invention is to provide an inspection apparatus with which it is possible to obtain images of a biological tissue without artefacts and with a wide field of vision.

A further object of the present invention is to provide an inspection apparatus that is easy to manufacture on an industrial scale, at competitive costs.

A further object of the present invention is to provide an inspection apparatus that is particularly suitable for observing or acquiring images relating to portions of organ, such as portions of skin.

A further object of the present invention is to provide an inspection apparatus that is particularly suitable for observing or acquiring images of the ocular fundus.

This aim and these objects, as well as other objects that will be apparent from the subsequent description and from the accompanying drawings, are achieved according to the invention by an apparatus for inspecting the ocular fundus according to claim 1 and the related dependent claims, set forth below.

In a general definition thereof, the apparatus according to the invention comprises:
- an illuminator adapted to provide an illuminating light beam to illuminate a portion of said biological tissue. The aforesaid illuminating beam is shaped so that at least a portion thereof has a line-shaped section;
- one or more lenses adapted to focus the illuminating beam on the biological tissue. During operation of said apparatus, the illuminating beam illuminates a line-shaped region of biological tissue that extends along a main extension direction;
- a scanning assembly adapted to perform optical scans of the biological tissue by moving the illuminating beam projected by the illuminator on the biological tissue, along a scanning direction substantially perpendicular to the main extension direction of the line-shaped region of biological tissue illuminated by the illuminating beam;
- acquisition means adapted to receive reflected light from the biological tissue to acquire images of the biological tissue or to allow an observer to observe said biological tissue.

According to the invention, the scanning assembly comprises:
- a fixed support;
- a first oscillating group comprising a first mobile arm and a mirror fixed to said first mobile arm and adapted to receive and divert the illuminating beam projected by the illuminator. The first mobile arm is linked with the fixed support through one or more first joints configured so as to allow the first mobile arm to move with respect to the fixed support with an oscillating rotation movement about a first rotation axis;
- a second oscillating group comprising a second mobile arm, a first lens and a diaphragm comprising a slot-shaped opening. The first lens and the diaphragm are fixed to the second mobile arm and are adapted to receive the reflected light from said biological tissue. The second mobile arm is linked to the fixed support through one or more second joints configured so as to allow the second mobile arm to move with respect to the fixed support with an oscillating rotation movement about a second rotation axis;
- mechanical transmission means adapted to mutually link the first and second mobile arm. The mechanical transmission means are configured so as to synchronize the oscillating movements of said first and second mobile arm.

According to an embodiment, the inspection apparatus comprises a second lens adapted to focus the illuminating beam projected by the illuminator on the biological tissue. During operation of said apparatus, the aforesaid second lens is positioned between said scanning assembly and said biological tissue. Said second lens contributes to optically conjugate the portion of illuminating beam having a line-shaped section with the region of biological tissue illuminated by said illuminating beam. In this way, the region of biological tissue illuminated is also line-shaped.

According to an embodiment, the inspection apparatus comprises a second lens and a third lens adapted to focus the illuminating beam projected by the illuminator on the biological tissue and an optical conjugation surface arranged between said second and third lens. During operation of said apparatus, the aforesaid second and third lens are positioned between said scanning assembly and said biological tissue, while the aforesaid optical conjugation surface is optically conjugated with said biological tissue.

Preferably, when the inspection apparatus is configured to inspect the retina of an eye, the aforesaid second and third lens are arranged so as to optically conjugate the pupil of the eye with a region of the inspection apparatus in which the mirror and the first lens of the scanning assembly are arranged.

Preferably, the first joints are configured as elastic joints and comprise at least a pair of elastically deformable first laminae fixed to the fixed support and to the first mobile arm. The aforesaid first elastically deformable laminae are arranged along mutually crossed extension directions.

Preferably, the second joints are configured as elastic joints and comprise at least a pair of elastically deformable second laminae fixed to the fixed support and to the second mobile arm. The second laminae are arranged along mutually crossed extension directions.

According to an embodiment of the invention, the mechanical transmission means comprise at least a rod rotationally linked with said first mobile arm and with the second mobile arm.

According to a further embodiment of the invention, the mechanical transmission means comprise at least an elastically deformable third lamina fixed to the first mobile arm and to the second mobile arm.

Preferably, the mechanical transmission means are arranged so that, when the first mobile arm moves with a first rotation angle about the respective first rotation axis, the second mobile arm moves (in a manner synchronized with the first arm) with a second rotation angle about the respective second rotation axis. Advantageously, the aforesaid second rotation angle is much wider than (approximately double) said first rotation angle.

Preferably, the scanning assembly comprises at least a spring having ends linked with the fixed support and with the first mobile arm or with the second mobile arm.

Figure 2:
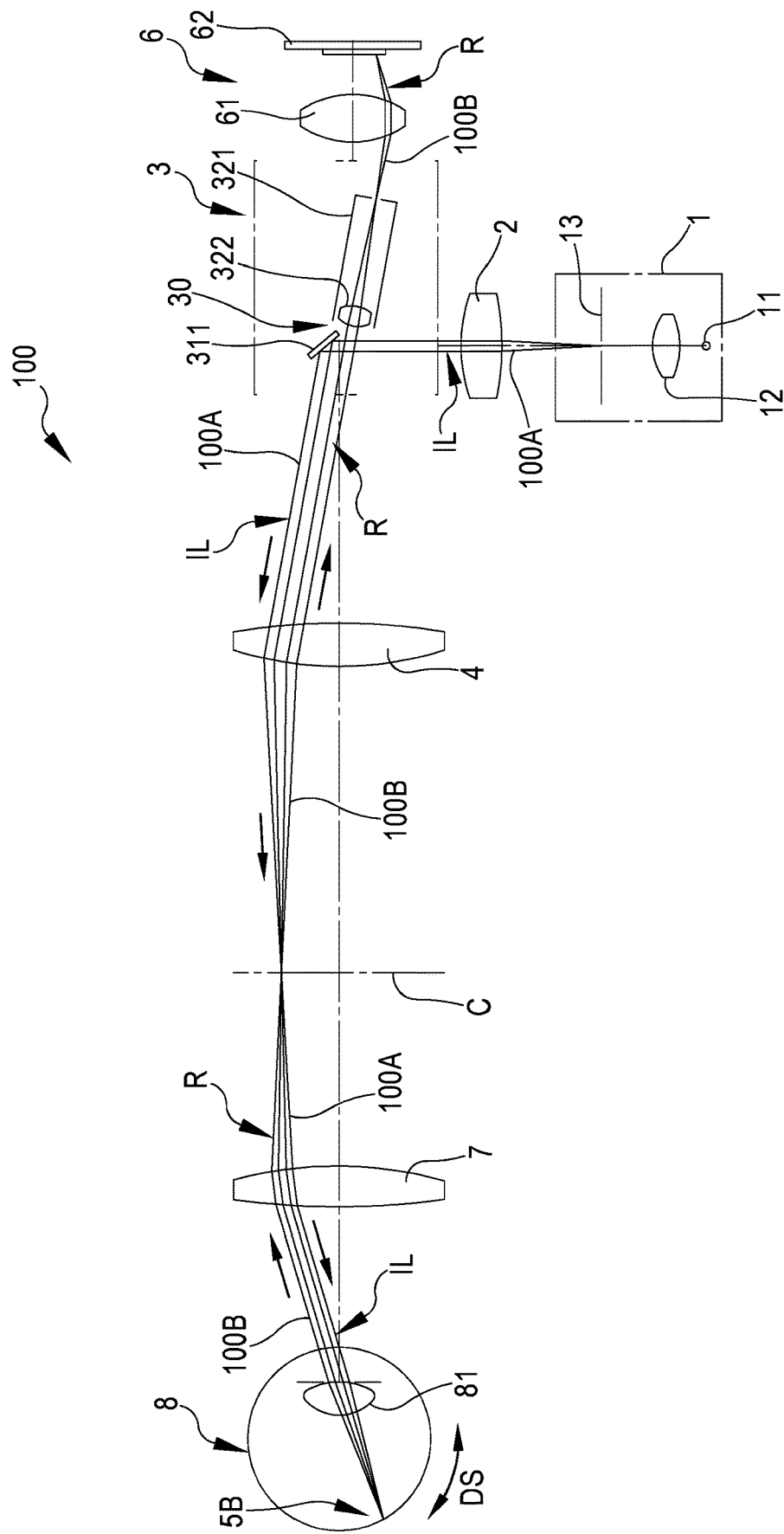
Figure 3:
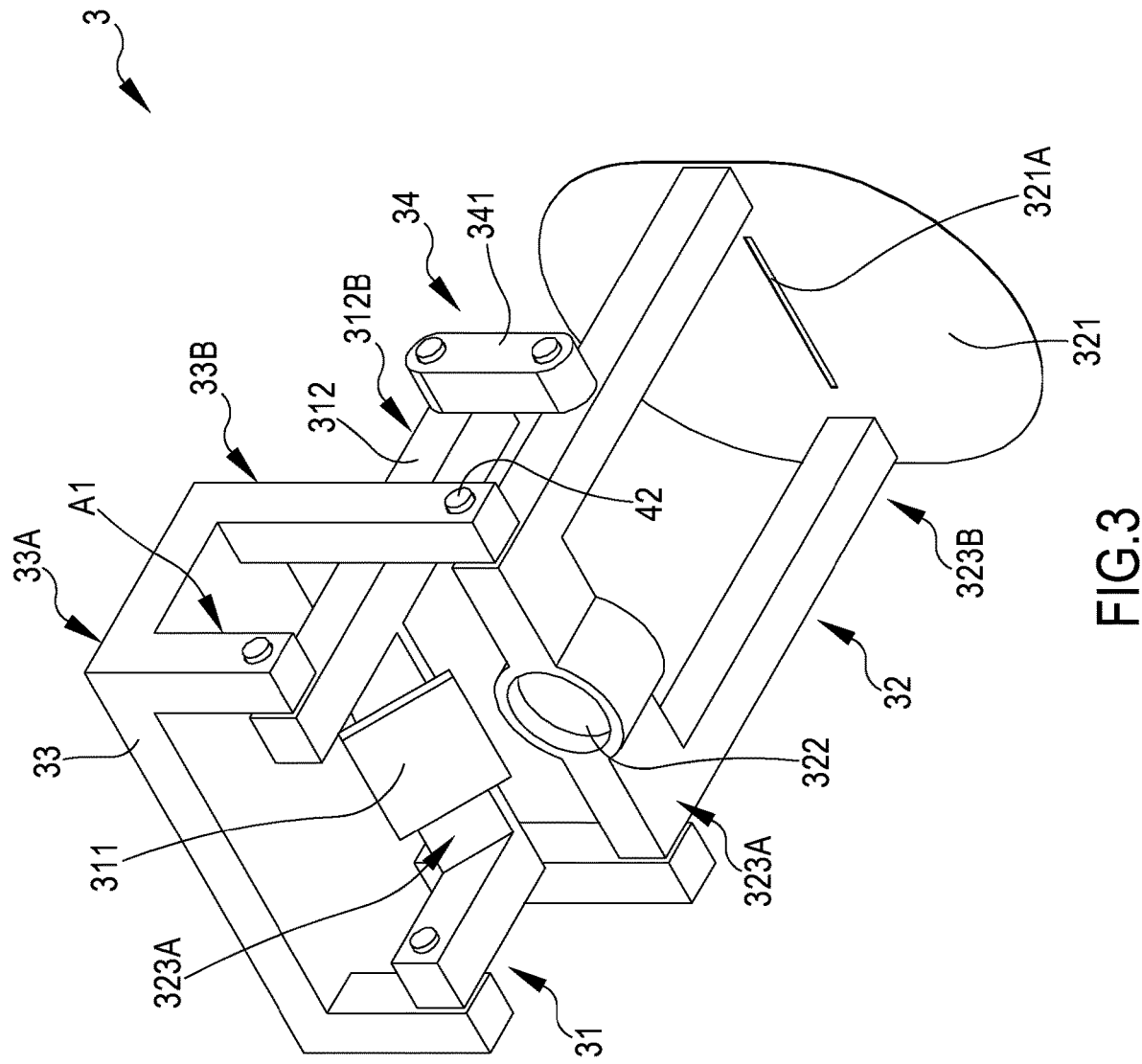
Figure 4:
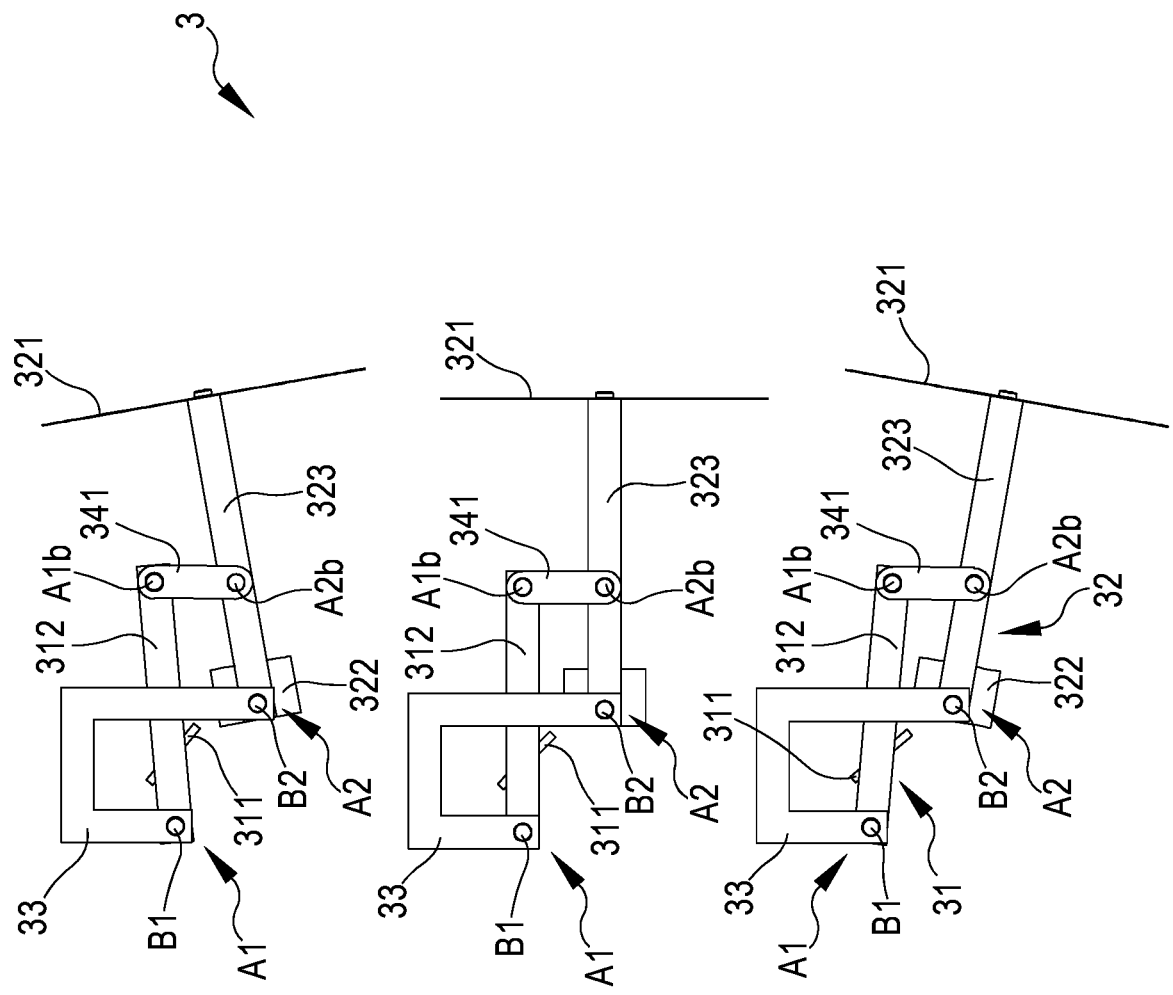
Figure 4A:
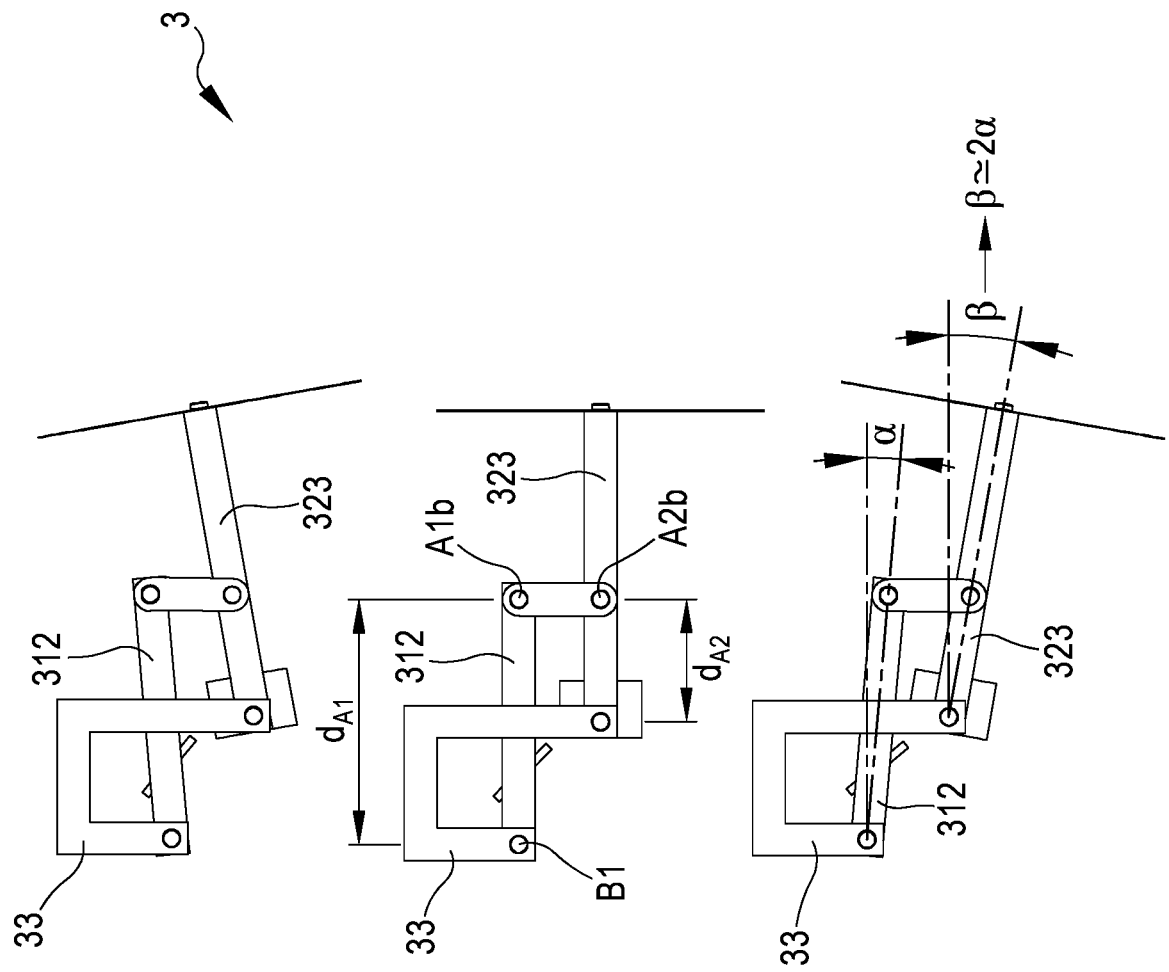

Further features and advantages of the inspection apparatus according to the invention can be better understood by referring to the description set forth below and to the accompanying figures, provided purely for non-limiting illustrative purposes, wherein:

FIG. 1 schematically illustrates the inspection apparatus according to the invention in a first embodiment thereof; and FIG. 2 schematically illustrates the inspection apparatus according to the invention in a further embodiment thereof; and FIGS. 3-4, 4A schematically illustrate structure and operation of the scanning assembly included in the inspection apparatus according to the invention in an embodiment; and FIGS. 5-8 schematically illustrate structure and operation of the scanning assembly included in the inspection apparatus according to the invention in a further embodiment.

With reference to FIG. 1, the present invention refers to a line-scanning confocal inspection apparatus 100.

The inspection apparatus 100 according to the invention is particularly suitable for observing biological tissue or for acquiring images relating to biological tissue.

In some embodiments thereof, the inspection apparatus 100 can be configured to observe or acquire images of the ocular fundus, i.e., to operate as a "fundus camera".

In other embodiments thereof, the inspection apparatus 100 can be configured to observe or acquire images of a portion of organ (such as a portion of skin).

The apparatus 100 comprises an illuminator 1 adapted to provide an illuminating light beam IL to illuminate a portion of biological tissue 5, 51.

The inspection apparatus 100 comprises an optical illumination path 100A, along which the illuminating light beam IL, projected by the illuminator 1, reaches the biological tissue 5, 51. During use of the apparatus 100, the optical path 100A therefore extends from the illuminator 1 to this biological tissue.

The illuminator 1 is configured to supply an illuminating beam IL shaped so that at least a portion of this illuminating beam has a line-shaped section.

For clarity, it is specified that the term "line-shaped section" of the illuminating beam IL identifies a section of the illuminating beam IL (along a plane with a section perpendicular to the illuminating beam) having a greatly elongated shape with a much larger main longitudinal dimension with respect to a transverse dimension, perpendicular with respect to said longitudinal dimension.

Therefore, during operation of said apparatus, the illuminating beam IL illuminates a line-shaped region 5B of biological tissue extending along a main extension direction AE.

Preferably, the illuminator 1 comprises at least a light source 11, for example comprising at least an LED (Light Emitting Diode).

According to a preferred embodiment, the illuminator 1 also comprises a collimating lens 12 and an illumination diaphragm 13 operatively coupled with said light source.

Advantageously, the illumination diaphragm 13 is provided with an elongated slit-shaped opening (for example rectilinear or slightly curved) with much smaller width with respect to the length.

In this way, the output illuminating beam I, supplied by the illuminator 11, has a line-shaped section at least in the portion thereof coinciding with the section of the opening of the illumination diaphragm 13.

The illuminator 1 could be produced according to other solutions (not illustrated).

For example, the aforesaid light source could itself be configured to supply a luminous line-shaped illuminating beam IL. An example of source of this type could be a straight incandescent filament, or a row of LED emitters in close proximity to one another.

According to a further example, the illuminator 1 could comprise a mirror having a reflecting surface of straight elongated shape, with much smaller width with respect to its length. In this way, the output illuminating beam I, supplied by the illuminator, would have a line-shaped section substantially coinciding with the reflecting surface of the aforesaid mirror.

Further examples of embodiment of the illuminator 1 are possible, according to requirements.

The apparatus 100 comprises acquisition means 6 adapted to receive reflected light R from R the biological tissue 5, 51 to acquire images thereof or to allow an observer to observe it (or to implement both these functions).

The apparatus 100 comprises an optical imaging path 100B, along which the reflected light R from the biological tissue reaches the acquisition means 6. During use of the apparatus 1, the optical path 100B therefore extends from the biological tissue 5, 51 to the acquisition means 6.

Preferably, the acquisition means 6 comprise a two-dimensional sensor 62, for example of CCD or C-MOS type. This two-dimensional sensor is advantageously arranged so as to receive the light R on a receiving surface and allow direct acquisition of two-dimensional images of the biological tissue 5, 51.

Preferably, the acquisition means 6 comprise a relay lens 61 adapted to convey, with a suitable magnifying factor, a conjugated image of the biological tissue 5, 51 in a new conjugated image on the receiving surface of the two-dimensional sensor 62. The relay lens 61 can be constructed as single lens or assembly of lenses.

For greater clarity it is specified that, within the scope of the present invention, the definition "optically conjugated" identifies positioning in the exact optical conjugation position or very close (with respect to the lengths of the optical paths of the apparatus 100) to the exact optical conjugation position.

According to some embodiments of the invention, in place of the two-dimensional sensor 62, the acquisition means 6 comprise an ocular (not illustrated) arranged so as to allow an operator to directly observe an image of the biological tissue.

According to further embodiments of the invention, the acquisition means 6 comprise an ocular, an acquisition group comprising the relay lens 62 and the two-dimensional sensor 61, illustrated above, and one or more mobile mirrors or beam splitters arranged so as to selectively divert the reflected light from the biological tissue toward the ocular or this acquisition group. In this way, an operator can select a mode of direct observation of the biological tissue or the acquisition of images thereof.

According to the invention, the inspection apparatus 100 comprises a scanning assembly 3 adapted to carry out periodic optical scans of the biological tissue. Each optical scan is carried out by moving the illuminating beam IL projected by the illuminator 1 on the biological tissue, along a scanning direction DS (FIG. 1).

Advantageously, the scanning direction DS is substantially perpendicular to the main extension direction AE of the region 5B of biological tissue (line-shaped) illuminated by the illuminating beam I.

Due to the scanning assembly 3, the line-shaped region 5B of biological tissue illuminated by the illuminator 1 on the biological tissue moves, during an optical scan, along the surface of the biological tissue 5, 51 according to the scanning direction DS.

To direct the illuminating beam IL toward the biological tissue, the scanning assembly 3 advantageously comprises a mirror 311 adapted to receive and divert the aforesaid illuminating beam along the optical illumination path 100A.

As will be more apparent below, the scanning assembly 3 is arranged so that the mirror 311 moves with an oscillating rotation movement that determines scanning of the beam IL on the biological tissue 5, 51, according to the scanning direction DS.

Advantageously, the scanning assembly 3 also has the function of directing at least part of the reflected light R from the biological tissue along the optical imaging path 100B, towards the acquisition means 6 and the function of filtering the reflected light R to eliminate at least part of the parasitic light coming from other zones of the biological tissue, other than the focus surface. To this end, the scanning assembly 3 advantageously comprises a first lens 322 and a confocal diaphragm 321.

The first lens 322 is adapted to receive the reflected light R from the biological tissue and direct it towards the confocal diaphragm 321, along the optical imaging path 100B. The lens 322 helps to create a conjugated image of the biological tissue, in the zone in which the confocal diaphragm 321 is positioned.

The confocal diaphragm 321 is arranged so as to be, during operation of the inspection apparatus, optically conjugated with the surface 5, 51 of the biological tissue.

The confocal diaphragm 321 is provided with a linear slot-shaped opening 321A with much smaller width with respect to the length.

During use, the opening 321A of the confocal diaphragm 321 is substantially conjugated with the region 5B of biological tissue illuminated by the illuminating beam I.

As will be more apparent below, the scanning assembly 3 is arranged so that the assembly containing the first lens 322 and the confocal diaphragm 321 moves with an oscillating rotation movement synchronized with the oscillating rotation movement of the mirror 311.

This synchronized movement advantageously allows optical conjugation between the opening 321A of the confocal diaphragm 321 and the portion 5B of biological tissue illuminated by the illuminating beam I to be maintained for the entire duration of the scan by the scanning assembly 3.

Advantageously, the first lens 322 and the confocal diaphragm 321 are arranged respectively in distal and proximal position with respect to the acquisition means 6, along the optical imaging path 100B.

Preferably, the confocal diaphragm 321 is positioned at or close to the focal point of the first lens 322.

The solution illustrated above offers relevant advantages.

Given that the first lens 322 moves together with the confocal diaphragm 321, it is possible to maintain the beam of reflected light R from the biological tissue 5, 51 coaxial with the axis of the lens, for the entire duration of the scanning movement. In this way any optical distortions introduced by the lens 322 are reduced, even in the case of wide scanning movements. This is important as any optical distortions could make it impossible to maintain the confocal diaphragm and the region 5B of biological tissue illuminated by the illuminating beam IL in a condition of optical conjugation, during the scanning movement.

A further advantage derives from the fact that it is possible to reduce any optical aberrations and hence improve the quality of the image of the biological tissue scanned, given that the beam R of reflected light from the biological tissue 5, 51 is constantly maintained coaxial with the axis of the first lens 322. The lens 322 can thus be produced with relatively simple and inexpensive construction solutions which nonetheless allow high quality images of the biological tissue 5, 51 to be obtained.

According to some embodiments (not illustrated), the lens 322 can be simply constructed as a double or as a triple lens.

Preferably, the confocal diaphragm 321 has a shape elongated along a direction perpendicular to the main extension direction of its opening 321A.

For example, the confocal diaphragm 321 could have an oval, rectangular or, more in general, an elongated shape, with a main longitudinal axis substantially perpendicular to the main extension direction of its opening 321A.

This solution makes it possible to prevent any parasitic light from reaching the acquisition means 6 directly, beyond the edges of the diaphragm 321, when the scanning movement performed by the scanning assembly 6 reaches its points of maximum amplitude.

In this way, the acquisition means 6 only receive the light passing through the opening 321A of the confocal diaphragm 321.

According to an alternative variant of embodiment of the invention (not illustrated), the scanning assembly 6 comprises an opaque tube mounted between the first lens 322 and the confocal diaphragm 321.

Preferably, this opaque tube has a substantially circular end positioned in proximity of the first lens 322 and a substantially rectangular opposite end positioned in proximity of the confocal diaphragm 321.

This solution also makes it possible to prevent any parasitic light from reaching the acquisition means 6 directly. In this case, the confocal diaphragm 321 can have smaller dimensions.

According to the invention, the inspection apparatus 100 comprises one or more lenses adapted to focus the illuminating beam IL on said biological tissue.

FIG. 1 illustrates an embodiment of the inspection apparatus 100 particularly suitable for observing or acquiring images relating to a portion of organ 5, such as a portion of skin.

According to this embodiment, the inspection apparatus 100 comprises a second lens 4 (produced as single lens or group of lenses close to one another) adapted to focus the illuminating beam IL on the biological tissue 5.

Preferably, the second lens 4 is positioned between the scanning assembly 3 and the region 5B of biological tissue illuminated by the illuminating beam I, during operation of the inspection apparatus.

The second lens 4 (possibly in cooperation with a further lens 2 described below) optically conjugates the biological tissue 5 with the zone of the illuminating beam IL in which this illuminating beam has a line-shaped (long and narrow) section.

Due to this optical conjugation, the image of the line-shaped section of the illuminating beam IL is projected onto the biological tissue 5. In this way, a line-shaped (long and narrow) region of biological tissue 5B corresponding to the image of the line-shaped section of the illuminating beam I is illuminated.

FIG. 2 illustrates an embodiment of the inspection apparatus 100 particularly suitable for observing or acquiring images relating to a portion of retina 51 of the eye 8 of a patient.

According to this embodiment, the inspection apparatus 100 comprises a second lens 4 and a third lens 7 (each produced as single lens or group of lenses) adapted to focus the illuminating beam IL on the retina 51 and a conjugation surface C arranged between said second and third lens.

Preferably, the second lens 4 and the third lens 7 are positioned between the scanning assembly 3 and the region 5B of retina illuminated by the illuminating beam IL, during operation of the inspection apparatus.

Preferably, the conjugation surface C is arranged so as to be optically conjugated with the region 5B of retina illuminated by the illuminating beam I, during operation of the inspection apparatus.

Preferably, the second lens 4 and the third lens 7 are arranged so as to optically conjugate the pupil 81 of the eye with a region 30 of the inspection apparatus in which the mirror 311 and the first lens 322 included in the scanning assembly 3 (FIG. 2) are arranged. In this way, due to the movement imparted by the scanning assembly 3, the illuminating beam IL and the beam of reflected light R at the level of the retina 51 oscillate angularly about a point placed more or less in the centre of the pupil 81.

The conjugation of the pupil of the eye with the region 30 of the scanning assembly 3 allows the apparatus 100 to illuminate and acquire images of a relatively large portion of retina, through a relatively small section of the pupil 81 of the eye.

The angular oscillation of the beams IL and R more or less about the centre of the pupil ensures the passage of these light beams towards or away from this relatively large portion of retina, even if the pupil 81 has a limited section.

Preferably, the inspection apparatus 100 comprises a fourth lens 2 adapted to focus the illuminating beam IL on the biological tissue 5, 51 in cooperation with the lenses 4, 7 described above.

Preferably, the fourth lens 2 is arranged between the illuminator 1 and the scanning assembly 3 along the optical illumination path 100A.

Preferably, the fourth lens 2 is arranged so as to have its focal point on or close to the line-shaped section of the illuminating beam I.

General operation of the inspection apparatus 100 (in the embodiments of FIGS. 1 and 2) is now described in greater detail.

The illuminating light beam IL projected by the illuminator 1 passes through the focusing lens 2 and reaches the mirror 311 of the scanning assembly 3.

The illuminating beam IL is scanned by the scanning assembly 3 through the oscillating rotation movement of the mirror 311 towards the lenses 4 (and possibly 7) which focus it on the biological tissue 5, 51.

On the biological tissue 5, 51, the illuminated portion 5B consists of the image of the linear section of the illuminating beam IL projected by the illuminator 1. This illuminated portion, in the shape of a luminous line, moves along the biological tissue 5, 51 according to a scanning direction DS imparted by the scanning assembly 3. The scanning direction DS is substantially perpendicular to the extension axis AE of the region 5B of biological tissue illuminated, in the shape of a luminous line.

The reflected light R from the biological tissue passes back through the lens 4 (and possibly 7) and is focused by the first lens 322 at the confocal diaphragm 321 which is optically conjugated with the portion 5B of biological tissue illuminated by the illuminating beam I.

The opening 321A of the confocal diaphragm 321 is conjugated with the illuminated linear zone 5B of biological tissue. The oscillating rotation movement of the confocal diaphragm 321 is synchronized with the oscillating movement of the mirror 311 so as to maintain the optical conjugation of the opening 321A with the region 5B of biological tissue illuminated, during the whole scanning movement.

The optical conjugation of the opening 321A with the zone 5B of biological tissue allows the reflected light R from the biological tissue to pass freely through this opening 321A. Instead, any parasitic light, coming from other zones of the biological tissue 5 different from the illuminated region 5B, hits the diaphragm 321 in different zones from the opening 321A and, consequently, is not able to pass towards the acquisition means 6. In this way, the probability of undesirable reflections, coming from objects positioned in different zones from the portion 5B of biological tissue or optically conjugated therewith and reaching the acquisition means 6, is greatly reduced.

The reflected light R from the biological tissue is hence directed towards the acquisition means 6 to form a two-dimensional image on the receiving surface of the two-dimensional sensor 61 or to form an image observable through the ocular included in these acquisition means.

Preferably, the inspection apparatus 100 also comprises a control unit (not illustrated) to control the operations thereof, for example to carry out functions of signal acquisition, data storage, data calculation functions and to generate control signals.

Preferably, the aforesaid control unit comprises at least a digital processing device, for example a microprocessor. For example, it can consist of a computer.

Advantageously, the control unit is operatively associated with the illuminator 1, the scanning assembly 3 and the acquisition means 6 and is able to control their operation by generating suitable control signals.

The control unit can be operatively associated with a man-machine interface for entering manual commands or for executing configuration or programming operations.

A particularly important aspect of the invention consists in the fact that the scanning assembly 3 comprises an innovative mechanism adapted to support the mirror 311, the first lens 322 and the confocal diaphragm 321 and to move them in a synchronized manner so that the confocal diaphragm 321 is always optically conjugated with the portion 5B of biological tissue illuminated by the illuminating beam I, during the optical scan.

According to the invention, the scanning assembly 3 comprises a fixed support 33.

According to the invention, the scanning assembly 3 comprises a first oscillating group 31 comprising a first mobile arm 312 and the mirror 311 fixed to said first mobile arm so as to be able to move in one piece therewith.

Preferably, the first mobile arm 312 is linked with the fixed support 33 through one or more first joints A1.

In the embodiments illustrated in the aforesaid figures, the first mobile arm 312 is linked with the fixed support 33 through a pair of first joints A1.

However, embodiments of the invention in which the first mobile arm 312 is linked with the fixed support 33 at a single joint A1 or at multiple joints A1 are possible.

According to the invention, the scanning assembly 3 comprises a second oscillating group 32 comprising a second mobile arm 323. The second oscillating group further comprises the first lens 322 and the confocal diaphragm 321 fixed to the second mobile arm 323 so as to be able to move in one piece therewith.

Preferably, the second mobile arm 323 is linked with the fixed support 33 through one or more second joints A2.

In the embodiments illustrated in the aforesaid figures, the second mobile arm 323 is linked with the fixed support 33 through a pair of second joints A2.

However, embodiments of the invention are possible in which the second mobile arm 322 is linked with the fixed support 33 at a single mechanical joint A2 or at multiple joints A2.

Preferably, the rotation axes B1, B2 of the mobile arms 312, 323 are mutually parallel.

As indicated above, the first lens 322 and the confocal diaphragm 321 are arranged respectively in distal and proximal position with respect to the acquisition means 6, along the optical imaging path 100B.

Preferably, the first lens 322 is fixed to the second mobile arm 323 in proximity of the second rotation axis A2 thereof with respect to the fixed support 33.

This solution makes it possible to reduce the lateral oscillations of the first lens 322 during the optical scan. This is particularly important in the case in which the inspection apparatus 2 is configured to inspect the ocular fundus.

Normally, in this case the entry zone of the reflected light R from the biological tissue 5, 51 in the first lens 322 is more or less optically conjugated with the pupil 81 of the eye. A reduced lateral oscillation in this entry zone makes it possible to achieve a reduced oscillation of the beam R at the level of the pupil of the eye and hence to obtain excellent images of the retina, even if the pupil is of limited size.

Preferably, the confocal diaphragm 321 is fixed to the mobile arm in a position spaced with respect to the first lens 322, advantageously at a distance approximately corresponding to the focal distance of the first lens 322.

Preferably, the first joints A1 are configured so as to allow the first mobile arm 312 to move with respect to said fixed support 33 with an oscillating rotation movement about a first rotation axis B1.

According to some embodiments of the invention (FIGS. 3-4), the first joints A1 each comprise a suitable linking pin destined to rotationally link the first arm 312 with the fixed support.

According to preferred embodiments of the invention (FIGS. 5-8), the first joints A1 are produced as elastic joints.

In this case, advantageously, each of them comprises a pair of first elastically deformable laminae L1. Each lamina L1 is advantageously fixed to the fixed support 33 and to the first mobile arm 312, preferably at the opposite ends thereof.

Figure 8:
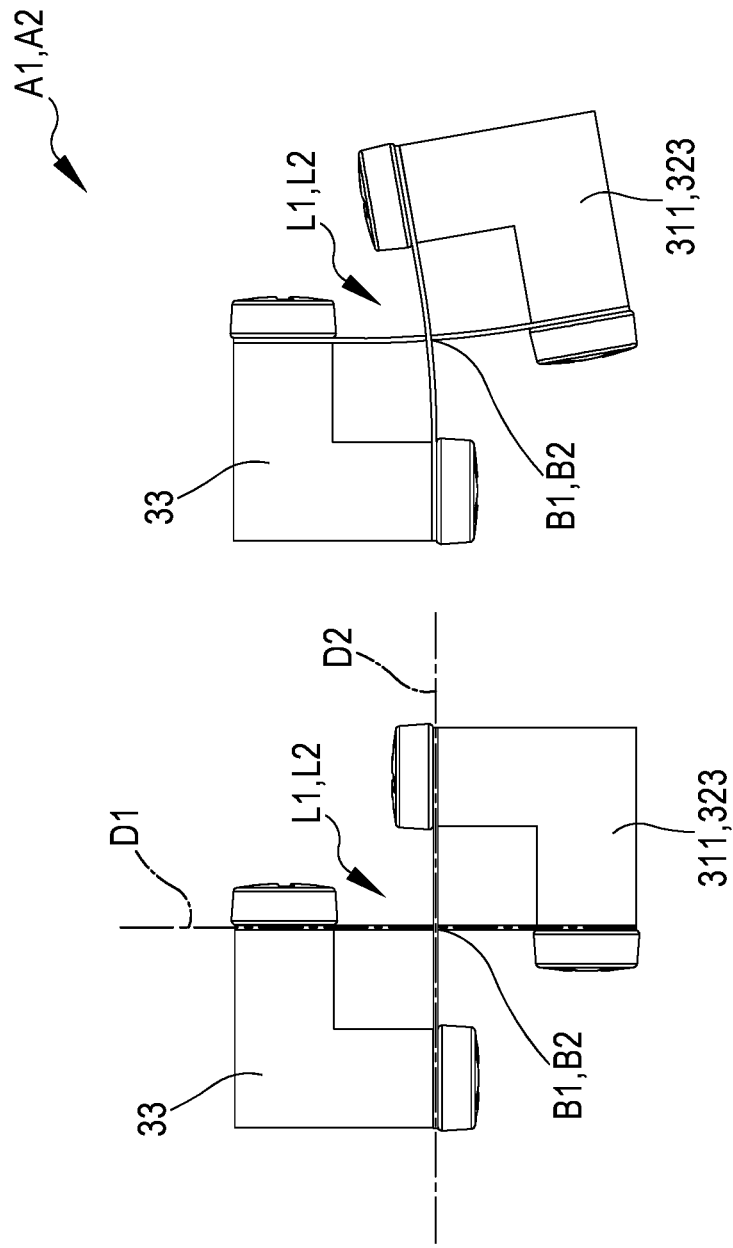

Preferably, the laminae L1 of each joint A1 are arranged along mutually crossing extension directions D1, D2 (preferably perpendicular), with reference to a common projection plane (FIG. 8).

Preferably, the laminae L1 of each joint A1 are arranged separated from but mutually close at a respective linking zone between the support 33 and the first mobile arm 312.

Preferably, the second joints A2 are configured so as to allow the second mobile arm 323 to move with respect to the fixed support 33 with an oscillating rotation movement about a second rotation axis B2.

According to some embodiments of the invention (FIGS. 3-4), the second joints A2 each comprise a suitable linking pin destined to rotationally link the first arm 312 with the fixed support.

According to preferred embodiments of the invention (FIGS. 5-8), the second joints A2 are produced as elastic joints.

Therefore, each of them comprises a pair of second elastically deformable laminae L2. Each lamina L2 is advantageously fixed to the fixed support 33 and to the second mobile arm 323, preferably at the opposite ends thereof.

Preferably, the laminae L2 of each joint A2 are arranged along mutually crossing extension directions D1, D2 (preferably perpendicular), with reference to a common projection plane (FIG. 8).

Preferably, the laminae L2 of each joint A2 are arranged separated from but adjacent to one another at a respective linking zone between the support 33 and the second mobile arm 312.

FIG. 8 schematically illustrates the operation of the joints A1, A2 when they each comprise a pair of elastically deformable laminae.

When the mobile arm 312 or 323 rotates, the laminae L1, L2 (mutually crossing) bend elastically, allowing the rotation of the mobile arm about an axis B1, B2 that passes more or less through the zone in which the two laminae mutually cross.

The use of elastically deformable laminae to produce the elastic joints A1, A2 offers considerable advantages.

Given that each pair of laminae L1, L2 is fixed to the fixed support 33 and to the respective mobile arm 312, 323 the presence of mechanical backlash and phenomena of wear are avoided.

The absence of backlash makes it possible to obtain optimal optical conjugation between the confocal diaphragm 321 and the portion 5B of biological tissue illuminated by the illuminating beam I. On the other hand, the absence of wear makes it possible to maintain optimal conjugation during the useful life of the inspection apparatus.

The elastic joints A1, A2 are also characterised by a total absence of friction between the parts. This makes it possible to reduce the mechanical power required to move the oscillating groups 31, 32 during the optical scan and facilitates control of the oscillating scanning movement.

The use of elastic joints A1, A2, also makes it possible to reduce noise deriving from the oscillating movement of the scanning assembly 6 and greatly simplifies the construction thereof.

According to the invention, the scanning assembly 3 comprises mechanical transmission means 34 adapted to mutually link the first and second mobile arm 31, 32.

Advantageously, the aforesaid motion transmission means are configured so as to mutually synchronize the oscillating movements of the first and second mobile arm 31, 32.

According to some embodiments of the invention (FIGS. 3-4), the mechanical transmission means 34 comprise at least a rod 341 rotationally linked with the first mobile arm 311 and with the second mobile arm 323.

Preferably (FIG. 4, 4A), the rod 341 is linked with the first mobile arm 311 and with the second mobile arm 323 through suitable joints A1$b$, A2$b$.

During the optical scanning movement, the rod 341 links the mobile arms 312 and 323 rotating with respect thereto at the joints A1$b$ and A2$b$. Consequently, it is capable of synchronizing the rotation movements of the oscillating groups 31 and 32.

According to preferred embodiments of the invention (FIGS. 5-7), the mechanical transmission means 34 comprise at least a third elastically deformable lamina L3 fixed to the first mobile arm 311 and to the second mobile arm 323.

The lamina L3 is advantageously fixed to the first mobile arm 312 and to the second mobile arm 323 in respective linking points P1, P2 (FIG. 7), preferably at the opposite ends thereof.

Durante the oscillating scanning movement, the lamina L3 bends elastically maintaining its length substantially unchanged. Consequently, it is capable of producing a high synchronization of the rotation movements of the two oscillating groups 31 and 32.

The use of an elastically deformable lamina L3 to produce the motion transmission means 34 offers advantages similar to those indicated above for the use the laminae L1, L2 to produce elastic joints A1, A2.

The arrangement of an elastically deformable lamina L3 is also simple and less expensive than the use of a rod.

As mentioned above, the transmission means 34 are arranged so as to synchronize the movement of the first and second mobile arm 312, 323.

Therefore, when the first mobile arm 311 moves with a first rotation angle $\alpha$ about the respective first rotation axis B1, the second mobile arm 323 moves with a second rotation angle $\beta$ about the second rotation axis B2.

The rotation angles α, β are mutually linked by a relation of proportionality that is substantially defined by the motion transmission means 34.

Preferably, at each oscillation movement of the mobile arms, the rotation angle β of the second mobile arm 323 is much wider (approximately double) than the rotation angle α of the first mobile arm 312 (FIG. 4A).

FIGS. 4, 4A schematically represent the oscillation movement of the scanning assembly 3 in three successive instants. During oscillation, while the first oscillating group 31 rotates with an angle α, the second oscillating group 32 rotates with an angle β. Preferably, the rotation angle β of the second mobile group 32 is substantially double with respect to the rotation angle α of the first mobile group 31.

According to the embodiments of FIGS. 3-4, this relation between the rotation angles α, β can be obtained by positioning the rotation axes of the joints A1$b$ and A2$b$ of the rod 341, at which it is linked with the mobile arms 312 and 323, respectively at a first distance $d_{41}$ and at a second distance $d_{42}$ from the corresponding rotation axes B1, B2 of the aforesaid mobile arms. Advantageously, the first distance dl is much greater (approximately double) than the second distance $d_{42}$ (FIG. 4A).

Figure 5:
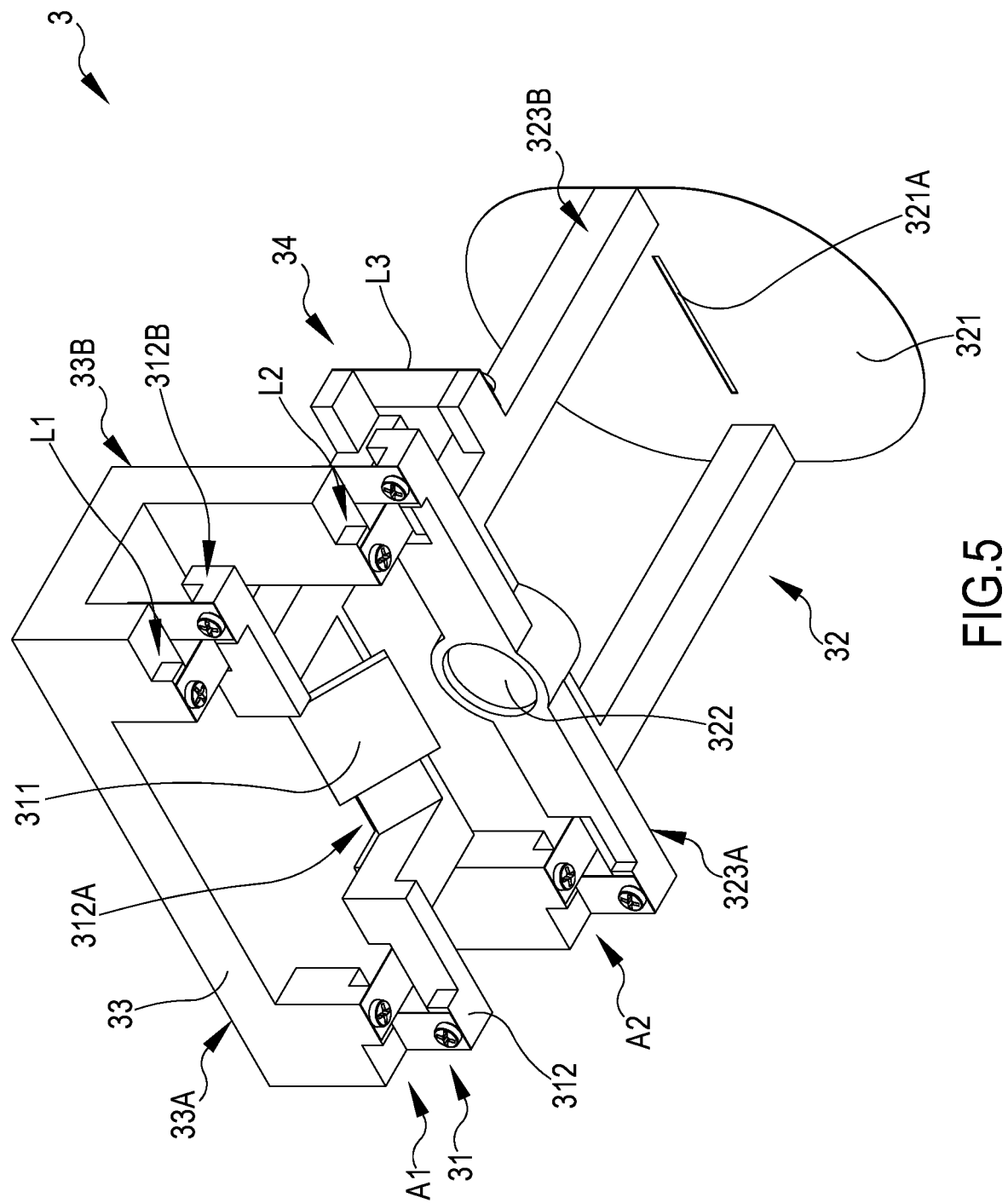
Figure 6:
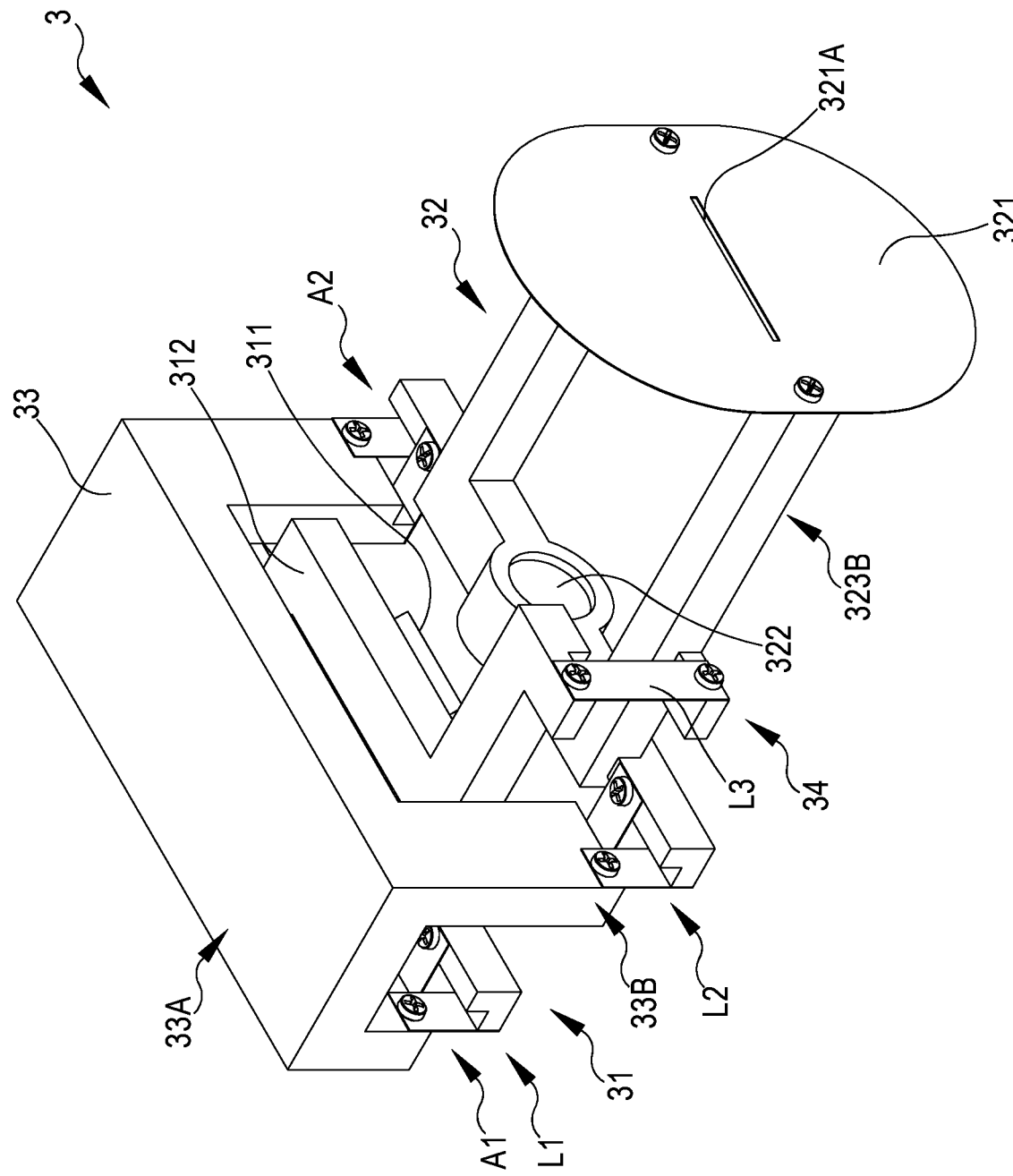
Figure 7:
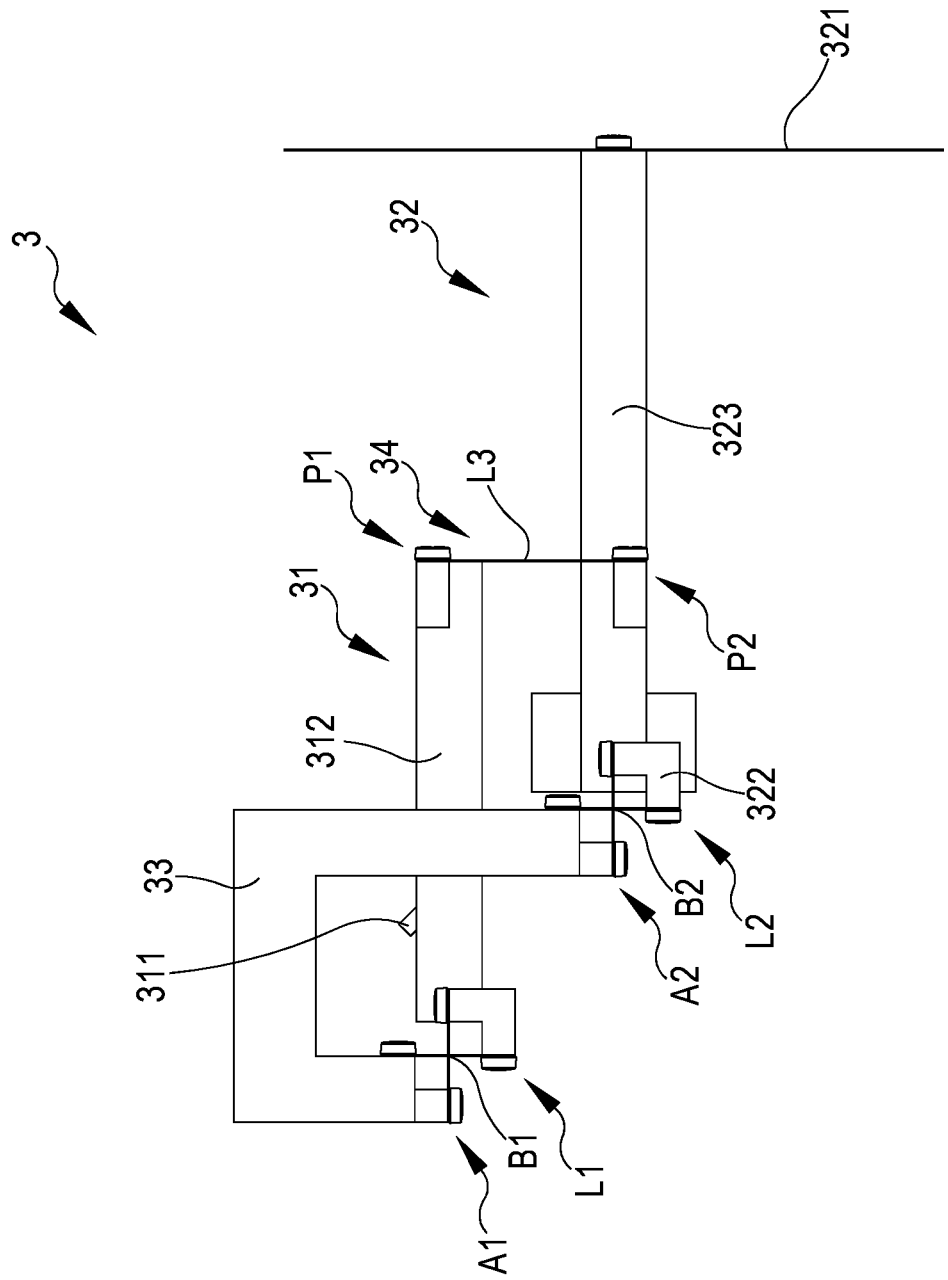

According to the embodiments of FIGS. 5-7, this relation between the rotation angles α, β can be obtained by positioning the fixing points P1, P2 of the elastic lamina L3, at which it is fixed to the mobile arms 312 and 323, respectively at a first distance and at a second distance from the corresponding rotation axes B1, B2 of the aforesaid mobile arms. Also in this case, the first distance is approximately double the second distance.

According to other embodiments of the invention (not illustrated), the motion transmission means could comprise a toothed belt, or an elastic cord or tape destined to transmit the motion between a pair of pulleys or circular sectors linked with the mobile arms 312, 323.

According to further embodiments of the invention (not illustrated), the motion transmission means could comprise a gear with toothed wheels suitably arranged, possibly coupling with a spring preload system to reduce mechanical backlash.

Preferably, the scanning assembly 3 comprises an actuator (not illustrated) adapted to supply mechanical energy to move the oscillating groups 31, 32.

In general, this actuator can be produced according to known solutions.

For example, it could comprise one or more coils fixed to the fixed support 33 and one or more mobile permanent magnets mounted on one of the oscillating groups 31 or 32.

According to a further example, this actuator could comprise a rotary electric motor together with a transmission that transforms the rotary movement of the motor into an oscillating movement, for example a crankshaft mechanism.

According to some embodiments, the scanning assembly 3 comprises at least a spring (not illustrated) having ends linked with the fixed support 33 and with the first mobile arm 311 or with the second mobile arm 323.

In this case, the first and second mobile arm 311, 323 are moved by the actuator advantageously at a resonance frequency characteristic of the scanning assembly 3.

This solution allows a considerable reduction in the mechanical power required to maintain the oscillation movement of the mobile arms 312, 323.

It is thus possible to move the oscillating groups 31, 32 with very simple and inexpensive electromagnetic actuators.

The inspection apparatus 100 according to the invention has considerable advantages with respect to the prior art.

In general, the inspection apparatus 100 has a very simple and compact structure and allows high quality images of the biological tissue 5, 51, without artefacts and with a wide field of vision, to be obtained.

In fact, with the inspection apparatus 100, it is possible to obtain optimal filtering of undesirable reflections and of other parasitic light capable of compromising the quality of the images.

The scanning assembly 3 is characterised by its extreme compactness and simple construction.

With the arrangement of a mobile focusing lens 322 it is possible to considerably simplify the optic of the inspection apparatus.

The embodiment of FIGS. 3-4, 4A is characterised by a high structural strength.

The embodiment of FIGS. 5-8 is characterised by high precision of movement, absence of noise and of mechanical backlash, long useful life and reduced energy consumption during the scanning movement.

The inspection apparatus 100 is easy to produce on an industrial scale, with considerable advantages in terms of limiting production costs.

It can be easily configured to observe or acquire images relating to portions of organ, such as portions of skin (embodiment of FIG. 1), or to observe or acquire images of the ocular fundus (embodiment of FIG. 2).

The invention claimed is:

1. An apparatus for inspecting a biological tissue, the apparatus comprising:
   an illuminator adapted to provide an illuminating light beam to illuminate a portion of said biological tissue, said illuminating beam being shaped so that at least a portion of said illuminating beam has a line-shaped section;
   one or more lenses adapted to focus said illuminating beam on said biological tissue, wherein during operation of said apparatus said illuminating beam illuminates a line-shaped region of biological tissue extending along a main extension direction;
   a scanning assembly adapted to perform optical scans of said biological tissue by moving the illuminating beam, projected by said illuminator on said biological tissue, along a scanning direction substantially perpendicular to the main extension direction of the line-shaped region of biological tissue illuminated by said illuminating beam;
   wherein the scanning assembly further comprises
      a fixed support,
      a first oscillating group comprising at least a first mobile arm and a mirror fixed to said first mobile arm and adapted to receive said illuminating beam, said first mobile arm being linked to said fixed support through one or more first joints allowing a rotation of said first mobile arm about a first rotation axis,
      a second oscillating group comprising at least a second mobile arm, a first lens and a diaphragm comprising a slot-shaped opening, said first lens and said diaphragm being fixed to said second mobile arm and adapted to receive reflected light by said biological tissue, said second mobile arm being linked to said fixed support through one or more second joints allowing a rotation of said second mobile arm about a second rotation axis, and
      mechanical transmission means adapted to mutually link said first and second mobile arms, said mechanical transmission means being configured to synchronize the oscillating rotation movements of said first and second mobile arms; and acquisition means adapted to receive reflected light by said biological tissue to acquire images of said biological tissue or to allow an operator to observe said biological tissue.

2. The apparatus of claim 1, comprising a second lens adapted to focus said illuminating beam on said biological tissue, wherein during operation of said apparatus said second lens is positioned between said scanning assembly and said biological tissue.

3. The apparatus of claim 1, comprising a second lens and a third lens adapted to focus said illuminating beam on said biological tissue and an optical conjugation surface between said second and third lenses, wherein during operation of said apparatus said second and third lenses are positioned between said scanning assembly, and said biological tissue and said optical conjugation surface are optically conjugated with said biological tissue.

4. The apparatus of claim 3, wherein when said apparatus is configured to inspect the retina of an eye, said second and third lens optically conjugate the pupil of the eye with a region of said apparatus, at which said mirror and said first lens of said scanning assembly are arranged.

5. The apparatus of claim 1, wherein said first joints comprise at least a pair of elastically deformable first lamina fixed to said fixed support and to said first mobile arm, said first lamina being arranged along mutually crossed extension directions.

6. The apparatus of claim 1, wherein said second joints comprise at least a pair of elastically deformable second lamina fixed to said fixed support and to said second mobile arm, said second lamina being arranged along mutually crossed extension directions.

7. The apparatus of claim 1, wherein said mechanical transmission means are arranged so that, when said first mobile arm moves with a first rotation angle about said first rotation axis, said second mobile arm moves with a second rotation angle about said second rotation axis, said second rotation angle being wider than said first rotation angle.

8. The apparatus of claim 1, wherein said mechanical transmission means comprise at least a rod rotationally linked with said first mobile arm and said second mobile arm.

9. The apparatus of claim 1, wherein said mechanical transmission means comprise at least an elastically deformable third lamina fixed to said first mobile arm and said second mobile arm.

10. The apparatus of claim 1, wherein the scanning assembly comprises at least a spring linked to said fixed support and to said first mobile arm.

11. The apparatus of claim 1, wherein the scanning assembly comprises at least a spring linked to said fixed support and to said second mobile arm.

12. The apparatus of claim 1, wherein said first lens is fixed to said second mobile arm in proximity of said second rotation axis.

* * * * *